United States Patent [19]
Fournier

[11] Patent Number: 6,155,990
[45] Date of Patent: Dec. 5, 2000

[54] CERVICAL SPECIMEN SELF-SAMPLING DEVICE (PAP TAMPON)

[76] Inventor: Arthur M. Fournier, P.O. Box 016700 (R700), Miami, Fla. 33101

[21] Appl. No.: 09/206,760

[22] Filed: Dec. 7, 1998

[51] Int. Cl.[7] .................................................. A61B 10/00
[52] U.S. Cl. ......................... 600/572; 600/562; 600/573; 604/330; 604/1
[58] Field of Search ..................... 600/562, 569, 600/572, 573; 604/1, 2, 11, 15, 18, 317, 328, 330, 358, 904

[56] References Cited

U.S. PATENT DOCUMENTS

| | | | |
|---|---|---|---|
| 2,847,000 | 8/1958 | Nieburgs | 600/572 |
| 3,857,384 | 12/1974 | Watson | 600/562 |
| 3,995,618 | 12/1976 | Kingsley et al. | 600/572 |
| 4,164,212 | 8/1979 | Schuster | 600/572 |
| 4,945,921 | 8/1990 | Okimoto | 600/572 |
| 4,952,204 | 8/1990 | Korteweg | 600/572 |
| 5,121,752 | 6/1992 | Canna | 600/572 |
| 5,339,828 | 8/1994 | Keating et al. | 600/572 |
| 5,445,164 | 8/1995 | Worthen et al. | 600/572 |
| 5,830,154 | 11/1998 | Goldstein et al. | 600/572 |

*Primary Examiner*—Cary O'Connor
*Assistant Examiner*—Charles Marmor, II

[57] ABSTRACT

A human female cervical specimen gathering device is disclosed which can be self administered by women. The device consists of a cardboard tube that houses a retractable sponge, The handle is adapted to allow it to serve as a screw-cap lid, once the device is inserted into a conical tube containing fixative or preservative. After transport to the lab the tube call easily be agitated to liberate cells, centrifuged, and prepared as a thin smear for cytology or DNA probes.

1 Claim, 2 Drawing Sheets

CERVICAL SPECIMEN SELF-SAMPLING DEVICE (PAP TAMPON)

BACKGROUND OF THE INVENTION

Screening for cervical cancer in women using cytological techniques has been possible for more than 40 years. The papanicolau test (pap test) has allowed for a significant reduction in mortality ill women from cervical cancer. Prior to the pap test, cervical cancer was the most common cause of cancer deaths in women. In countries where pap smears are available, mortality from cervical cancer is negligible.

In spite of this progress, there are several problems with the present technology. Conventional pap tests show a high percentage of smears of undetermined significance that requires further testing. This problem has led to the development of "thin prep" technology. Thin prep technology requires that cells be immersed in fixative and centrifuged prior to analysis. Other advances in diagnostic technology are the discovery of DNA probes for human papilloma virus (HFV), the causative agent of cervical cancer, and for chlamydia, a common infection in women. Tests for HPV may soon replace conventional pap smears as the initial screening test for cervical cancer. Collection of cytologic specimens currently requires a speculum examination which is frequently uncomfortable and embarrassing for women, It is also relatively expensive, since it requires the services of a physician or nurse practitioner. Finally, the specimen obtained is applied directly to a glass slide, which is not compatible with automated cytologic analysis or necessary for HPV assay. The same problems of discomfort, embarrassment, expense and processing also apply to the obtaining of specimens to diagnose vaginal infections such as candidiasis, gonorrhea, human papilloma virus and chlamydia.

Prior self sampling devices (described in the next section) were either designed prior to the invention of thin prep and HPV assay technologies or designed specifically to obtain a specimen in the setting of a conventional speculum examination. Given these problems, there is a need for an improved, inexpensive self sampling device which asymptomatic women can use in the privacy of their home that is adaptable to automated cytology methods (thin smear), HPV assay and microbial culture. This application (discloses just such an improvement.

PRIOR ART

Several previously disclosed self sampling devices have failed because they fail to protect the sample from vaginal secretions and contamination (U.S. Pat. Nos. 2,847,000; 3776,219; 3,857,384). Below are described previously disclosed devices that are designed to protect the sample from vaginal contamination.

U.S. Patent No. 5,121,752 discloses a self sampling device that utilizes a relatively large diameter hollow cylindrical speculum coupled with a mirror-guided hinged spatula. This device is not applicable for mass screening, since it is uncomfortable for many women to insert, and technically difficult for most women to manipulate in order to obtain an adequate specimen (to do this at home, it would require the manipulation of the speculum, the spatula, a mirror and a light source).

U.S. Patent No. 3,995,618 discloses a double barreled plastic tube with a sponge on one end for self-sampling of cervical tissues. This device has some of the features of this disclosure including its simplicity of use and ability to protect the specimen from vaginal contamination. However, its plastic construction increases its expense and is unnecessarily complicated, with an unwinding sponge which is dragged across an internal slide to obtain the specimen. It is also not biodegradable and is more difficult to dispose of than this disclosure. The device is therefore not designed to be inserted into a conical tube after the specimen is obtained, with the handle serving as the screw-cap seal—a feature which will allow the proposed device to adapt to thin smear cytologic technique and microbiologic culture and HPV assay. It should be noted that thin smear cytology, automated cytology and microbiologic assays such as PCR did not exist when U.S. Pat. No. 3,995,618 was disclosed.

U.S. Pat. No. 2,847,000 is the prototype cervical self sampling device. This device is designed to obtain cervical cytology specimens through a tanmpon-like device and then transfer the specimen to a slide enclosed within the tampon. This device never was put to clinical use. Its design is flawed because the cervical cells will adhere to the anterior portion of the sponge (3) in a position that will not be transferable to the slide (7). This device is not compatible with thin prep technology.

U.S Pat. No. 5,830,154 discloses a cylindrical tube with a slide attached to a screw cap allowing it to be immersed in fixative. It is not a self sampling device, although it could be modified slightly to be the receptacle of specimens obtained by this invention.

U.S. Pat. No. 4,945,921 discloses a vaginal self-sampling device designed exclusively to test vaginal pH. It cannot be used for cytologic or microbiological assay.

U.S. Pat. No. 4,952,204 discloses a swab with a handle enclosed in a sheath to protect the swab from contamination. The device was not designed for cervical self-sampling, nor is such an intent claimed—the purpose of the device is simply to maintain the sterility of the swab.

U.S. Pat. No. 5,339,828 discloses a device for obtaining specimens by trained clinicians through endoscopy. Tt is not practical or compatible with cervical self sampling.

U.S. Pat. No. 5,445,164, Worth et al describes an alternative approach to cervical self sampling, more elaborate in design than the present invention. Although this design addresses many of the same issues and problems of self sampling as the present device, it is designed to be mailed in after use, as opposed to being immediately immersed in fixative or preservative. This, at a minimum creates extra steps in handling and may interfere with the technique, sensitivity and specificity of thin prep cytology, Again, it should be noted that this device was invented prior to the FDA approval of thin prep cytology (1996).

U.S. Pat. No. 3,857,384 is a cervical self sampling device in which specimens are sampled directly onto a smear. It is thus not compatible with thin prep cytology.

U.S. Pat. No. 4,164,212 discloses a device for obtaining mucus to determine menstrual phase. This is a device designed to evaluate problems with fertility, not cervical cancer or vaginal infections.

SUMMARY OF THE INVENTION

Accordingly, the present invention comprises a tampon-like device that will allow for the self sampling of cervical specimens. The device will be inexpensive to produce, easy to destroy after use, and easy for women to use. It will allow for the safe transportation of the specimens to laboratories for analysis and is easily adaptable for centrifugation and thin-film preparation, or DNA probe for HPV, which is a technological improvement over the older direct preparation of a smear.

In a more limited application of this device, it can also be used to obtain specimens for culture or microbiologic assay. This will make it useful in the diagnosis of vaginal infections and for epidemiologic studies of sexually transmitted diseases.

DETAILED DESCRIPTION OF THE INVENTION

Figure 1:
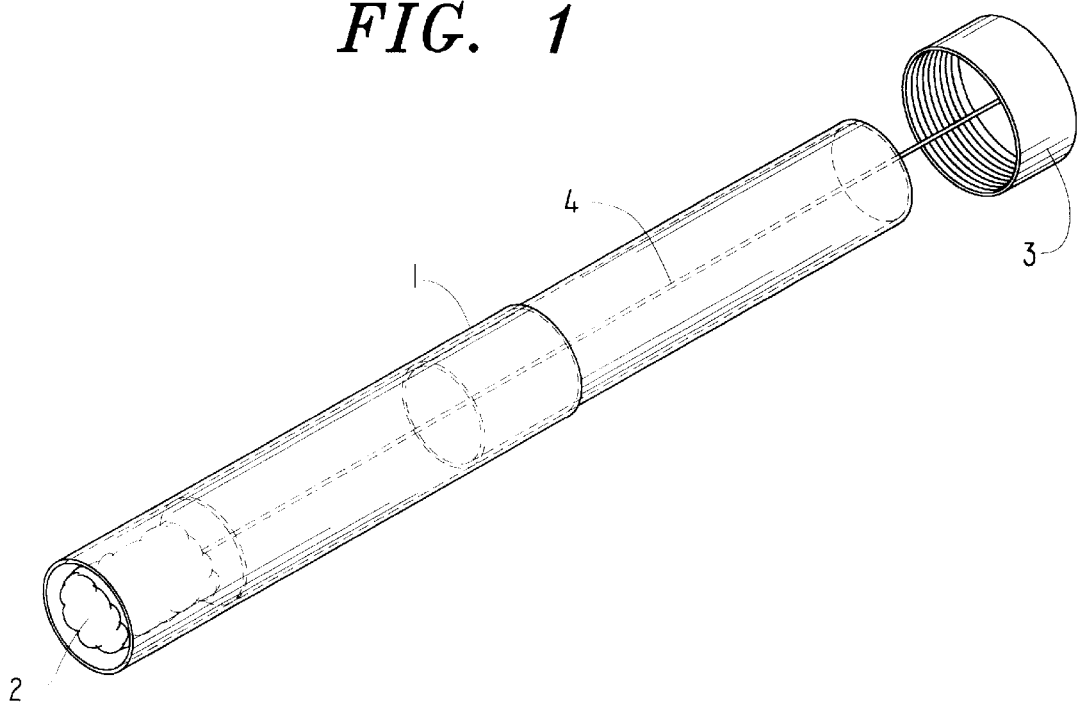
FIG. 1 is a perspective view of the self-sampling device, taken from one side and below.
Figure 2:
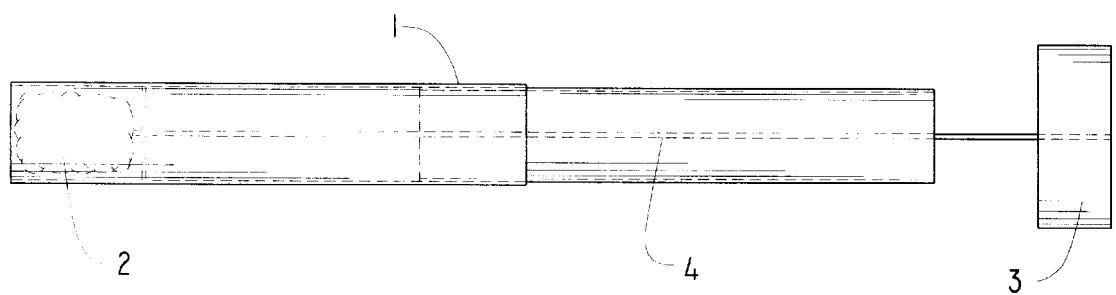
FIG. 2 is a cross-sectional view demonstrating the internal design.
Figure 3:
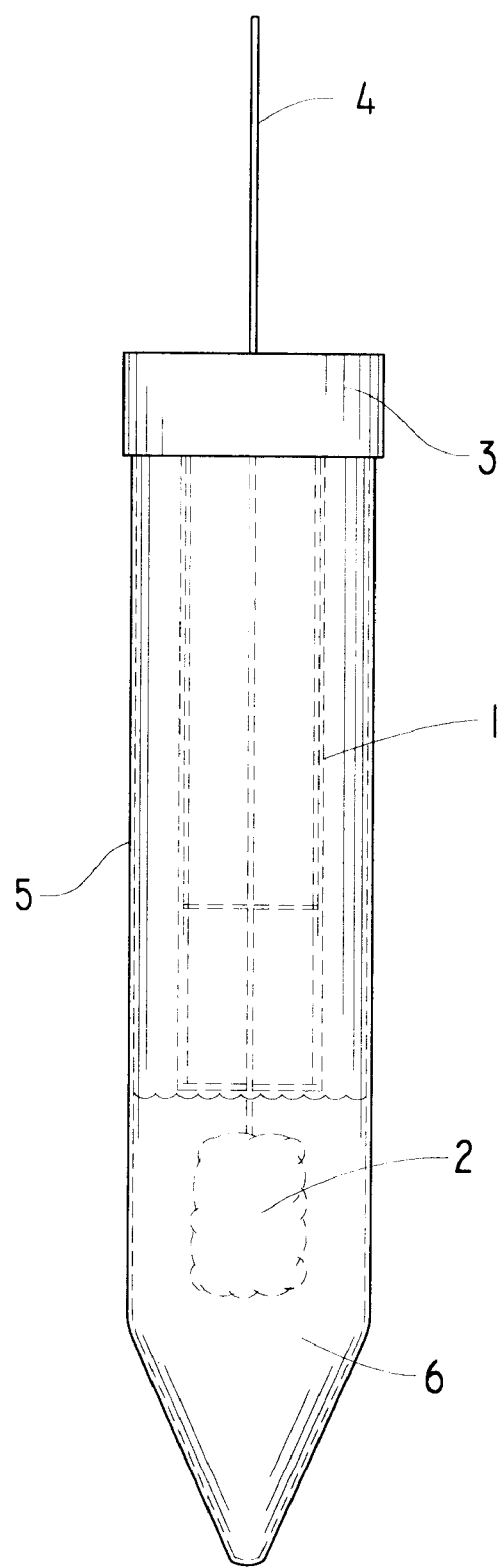
FIG. 3 is a diagram demonstrating how the device is designed to fit and seal a standard cylindrical tube, in order to process the specimen using thin-film cytology.

Please refer to FIGS. 1–3 for a complete understanding of this invention. The drawings represented the current best conceptualization of the design, alone is not to be construed as a restriction or limitation of its scope.

As can be seen in FIG. 1 and 2, the device is an assembled unit consisting of a "telescoping" cylindrical tampon-like cardboard sheath (1) which houses the specimen-gathering sponge (2). The sponge is attached to the screw-cap handle (3) by a square dowel (4) that perforates a rubber seal in the handle, The cylindrical tampon sheath (1) is constructed of medical-quality cardboard and coated with wax or Teflon to allow for minimal friction on insertion. With the "telescope" fully extended and the sponge housed in the anterior chamber of the sheath (1), the device is inserted into the vagina until resistance is met. By grasping the posterior end of the sheath (1) between the first two fingers and pressing on the handle (3) with the thumb, the sponge (2) will extend into the vaginal vault.

The sponge nay be composed of several possible materials, including, but not limited to cellulose, natural or artificial sponge material. The sponge should have good adherent and mildly abrasive qualities. The vacuum created by the sponge upon insertion should draw cells down from the cervical canal without the trauma that might be created by a traditional spatula. It also obviates the need for direct visualization of the cervical os After insertion of the sheath and extrusion or the sponge, the handle (3) is rotated to obtain the specimen and then retracted in order to return the sponge to the anterior chamber prior to removal. A rim on the inner tube and a groove on the inner surface of the outer tube will assure that the telescope mechanism does not collapse prior to the sponge returning to the anterior chamber.

The overall length of the device is 15 cm. The length of the sheath will be 13 cm when fully extended. The maximum width will be 1.5 cm. These dimensions will accommodate the standard vaginal depth of 12.7 cm for a mature woman, and are sufficiently narrow to allow for comfortable insertion. The device will collapse to 7 cm, allowing it to be easily inserted into a standard conical tube (5) of 11.5 cm in depth. The screw-cap handle is designed so that the cap will form a tight seal on the conical tube (5). The dowel (4) will extend above the handle (see FIG. 3), its length of protrusion fixed by the collapse of the telescope and the need for the sponge to be freely immersed in the fixative (6), The sponge will be immediately immersed in the fixative after removal of the device from the patient, avoiding problems associated with drying. Upon arrival at the laboratory, the device-fixative-tube will be agitated to liberate cells from the sponge, centrifuged and the supernatant discarded. The cellular contents will be removed and prepared as a thin-film slide for either manual or automated cytologic examination using conventional cytologic techniques. The device can then be disposed using "universal precautions" and incinerated, By simply changing the solution in the conical tube, the device can easily be adapted for culture, "wet mount", KOH prep for fungal examinations or PCR assays for chlamydia and human papilloma virus. Although the device is primarily designed for self-sampling of cytologic specimens, it may have wide applications in the diagnosis of vaginal infections, in conducting epidemiologic studies of sexually transmitted diseases or in comparing the utility of PCR assay for human papilloma virus to conventional cytology as a screening test for cervical cancer. While several embodiments of the inventive concept have been described, it is understood that the invention is not to be construed as limited thereby, and that suitable modifications and variations may be made without departing front the spirit and scope of the invention as described in the following claims.

What is claimed is:

1. A cervical self-sampling device for the self-sampling of culture material or specimens for use in thin smear cytology techniques, microbiologic assay, and epidemiologic studies, said device comprising:

a tampon-like telescoping cardboard tube;

an extrudable and retractable sponge housed within said telescoping cardboard tube, said sponge sized for the painless self-sampling of cervical specimens; and a handle attached to said sponge, the handle forming a screw cap for a standard conical tube for sealing and preserving a sample in a fixative contained within the tube.

* * * * *